US012665062B2

(12) United States Patent
Schrader et al.

(10) Patent No.: US 12,665,062 B2
(45) Date of Patent: Jun. 23, 2026

(54) PATIENT-LED PRESCRIPTION REFILL GROUPING SYSTEM AND METHOD

(71) Applicant: Outcome One, Inc., Orlando, FL (US)

(72) Inventors: Jeremy Richard Schrader, Webster, NY (US); Bipinkumar Ashokkumar Dubey, Pittsburgh, PA (US)

(73) Assignee: Outcomes One, Inc., Orlando, FL (US)

( * ) Notice: Subject to any disclaimer, the term of this patent is extended or adjusted under 35 U.S.C. 154(b) by 232 days.

(21) Appl. No.: 18/492,293

(22) Filed: Oct. 23, 2023

(65) Prior Publication Data

US 2024/0136038 A1    Apr. 25, 2024
US 2024/0233900 A9    Jul. 11, 2024

Related U.S. Application Data

(60) Provisional application No. 63/380,649, filed on Oct. 24, 2022.

(51) Int. Cl.
*G16H 20/10*        (2018.01)
*G16H 40/20*        (2018.01)

(52) U.S. Cl.
CPC .............. *G16H 20/10* (2018.01); *G16H 40/20* (2018.01)

(58) Field of Classification Search
CPC .............................. G16H 20/10; G16H 40/20
See application file for complete search history.

(56) References Cited

U.S. PATENT DOCUMENTS

| | | | | |
|---|---|---|---|---|
| 10,325,073 B1 * | 6/2019 | Ewing | .................... | G16H 10/60 |
| 10,552,575 B1 * | 2/2020 | Mohebbi | ................. | G06F 18/22 |

| | | | | |
|---|---|---|---|---|
| 11,074,998 B1 * | 7/2021 | Liotta | .................... | G16H 40/60 |
| 2007/0143132 A1 * | 6/2007 | Linne | ................. | G06Q 30/0278 |
| | | | | 705/306 |
| 2007/0143137 A1 * | 6/2007 | Ross | ..................... | G16H 20/10 |
| | | | | 600/300 |
| 2008/0077439 A1 * | 3/2008 | Guion | ................... | G16H 40/63 |
| | | | | 705/2 |
| 2008/0091468 A1 * | 4/2008 | Heidenreich | .......... | G16H 80/00 |
| | | | | 705/3 |

(Continued)

OTHER PUBLICATIONS

Payne K, Unni EJ, Jolley B. Impact of Dispensing Services in an Independent Community Pharmacy. Pharmacy (Basel). May 10, 2019;7(2):44. doi: 10.3390/pharmacy7020044. PMID: 31083334; PMCID: PMC6631564. (Year: 2019).*

(Continued)

*Primary Examiner* — Sun M Li
(74) *Attorney, Agent, or Firm* — Dawn-Marie Bey; Bey & Cotropia PLLC

(57)        ABSTRACT

A device and method may determine whether a patient is projected to run out of a first prescription medication within a first window extending a first number of days ahead of a current day. A device may determine whether the patient is eligible to receive a refill of one or more second prescription medications within a second window extending a second number of days from a day when the patient is projected to run out of the first prescription medication. A device may send an electronic message to the patient with an option of a refill order of the first prescription medication and the one or more second prescription medications and receives a refill order of one or both of the first prescription and the one or more second prescriptions.

13 Claims, 6 Drawing Sheets

(56) References Cited

U.S. PATENT DOCUMENTS

| | | | | | |
|---|---|---|---|---|---|
| 2008/0238666 | A1* | 10/2008 | Loncar | ................... | G16H 70/40 |
| | | | | | 715/810 |
| 2011/0184755 | A1* | 7/2011 | Yamaga | ................. | G06Q 10/00 |
| | | | | | 705/3 |
| 2012/0209619 | A1* | 8/2012 | Knotts | .............. | G06Q 10/0832 |
| | | | | | 705/2 |
| 2013/0090937 | A1* | 4/2013 | Wright | ................... | G16H 40/67 |
| | | | | | 705/2 |
| 2017/0004282 | A1* | 1/2017 | Scantland | .............. | G06Q 40/08 |
| 2018/0333860 | A1* | 11/2018 | Jamriska | ................. | G06Q 50/22 |
| 2018/0365385 | A1* | 12/2018 | Cooney | ................... | G16H 20/60 |
| 2021/0050081 | A1* | 2/2021 | Malkin | .............. | G06Q 30/0641 |
| 2021/0241892 | A1* | 8/2021 | Todd | ....................... | G16B 50/00 |
| 2022/0020462 | A1* | 1/2022 | Kim | ....................... | G06Q 50/26 |
| 2022/0036990 | A1* | 2/2022 | Todd | ....................... | G16H 20/10 |
| 2022/0399093 | A1* | 12/2022 | Stong | ................... | G06F 3/0482 |
| 2023/0197235 | A1* | 6/2023 | Lion | ....................... | G16H 20/13 |
| | | | | | 705/2 |

OTHER PUBLICATIONS

Peter ME, Zuckerman AD, Cherry E, Schlundt DG, Bonnet K, Shah N, Kelley TN. Exploring healthcare providers' experiences with specialty medication and limited distribution networks. PLoS One. Aug. 15, 2022;17(8):e0273040. doi: 10.1371/journal.pone. 0273040. PMID: 35969591; PMCID: PMC9377589. (Year: 2022).*

Marupuru S, Dhatt H, Bingham JM, Warholak T. Evaluation of a Novel Pharmacist-Delivered Adherence Improvement Service via Telehealth. Pharmacy (Basel). Aug. 17, 2021;9(3):140. doi: 10.3390/pharmacy9030140. PMID: 34449707; PMCID: PMC8396285. (Year: 2021).*

Tom Murphy, "Pharmacist shortages and heavy workloads challenge drugstores heading into their busy season," AP News online Oct. 7, 2023 (https://apnews.com/article/cvs-walgreens-pharmacists-drug-shortages-c7a94430a2c9d11779a684c2bcfc4c2c)(downloaded Mar. 22, 2024).

"Medication Overload: America's Other Drug Problem; How the drive to prescribe is harming older adults" Lown Institute, Apr. 2019 online (https://lowninstitute.org/projects/medication-overload-how-the-drive-to-prescribe-is-harming-older-americans/)(downloaded Mar. 22, 2024).

* cited by examiner

PATIENT-LED PRESCRIPTION REFILL GROUPING SYSTEM AND METHOD

CROSS-REFERENCE TO RELATED APPLICATIONS

The present application claims priority to similarly titled Provisional Patent Application Ser. No. 63/380,649, filed Oct. 24, 2023 which is incorporated herein by reference in its entirety.

BACKGROUND

Field of the Embodiments

Aspects of the present disclosure relate generally to systems and methods for organization and grouping of patient prescription refills, including methods and systems that give patients more control over timing of the refills of their prescriptions and/or other functionality and improve pharmacy efficiencies. Specifically, aspects of the present disclosure provide means for patients to select how to align the timing of their refills by, for example, selecting ahead of time which prescriptions will be refilled together.

Description of the Related Art

Medication organization tools generally operate by giving a pharmacist visibility to a patient's upcoming medication refills, allowing the pharmacist to group the medication refills so that they may be filled on the same day. The purpose of medication alignment is to reduce the number of trips a patient makes to the pharmacy and encourage better adherence to the patient's medication regimen by ensuring that the patient does not run out of medication.

Generally, pharmacists have used medication organization tools to "short-fill" a prescription in order to line the refill schedule of the prescription with the refill schedule of other medications prescribed to the patient. That is, a short-fill provides the patient with less than a full supply of the prescribed medication such that the patient will run out of the short-filled medication at the same time as another medication, thereby allowing both medications to be refilled at the same time in the next cycle.

For example, if a 90-day supply of a new medication is prescribed, a pharmacist using related medication organization tools may note that the patient is due for a refill of another medication in 15 days. Accordingly, the pharmacist would short-fill the new medication by providing a 15-day supply, then would complete fills of both medications on the next cycle.

After the initial short-fill, the two medications would be considered aligned, meaning that the medications could be filled and picked up by the patient together on an "anchor date." However, achieving such alignment depends on the refill cycles of the two medications, as well as the patient's insurance, the patient's adherence to the medication regimen, and various other patient factors that may not be known to the pharmacist.

Under the best of circumstances, related medication organization tools require an in-depth level of review by a pharmacist or trained pharmacy staff to determine whether and how to attempt to align the refill schedules of various patient medications. Even if medication alignment is achieved, the alignment may be broken at any time, due to, for example, a change in the patient's prescriptions, a patient's admission to a hospital, or due to the patient filling the prescription at another pharmacy, for example due to travel.

Additional challenges with related medication organization tools are based on the fact that certain medications, such as drops, ointments, or insulin, may not be discretely portioned and/or may be used at different rates by different patients, as needed. In such cases, the rate of use of the medication may not be known to the pharmacist engaging in the medication alignment analysis, making it difficult to predict when a refill of such medications would be needed.

Finally, the implementation of medication alignment may create additional labor costs for pharmacies up front, without necessarily resulting in any efficiencies. For example, a short-fill of a prescription doubles the labor cost to the pharmacy of filling that prescription because the pharmacist first fills the short-fill and then fills the remainder of the prescription on the anchor date, in order to align with another medication. In this case, the labor cost is doubled in order to achieve medication alignment, yet any business efficiencies arising from the medication alignment are not guaranteed because, as noted above, the patient may not adhere to the medication regimen or may refill the aligned medications at a different pharmacy next time. Short-filling practices may introduce additional inefficiencies, such as putting a patient in a position where a balance of medication is left on a prescription and may go unused and/or requiring additional packaging and supplies. Such challenges to medication alignment are addressed by the present disclosure, which removes the burdens of medication alignment analysis from the pharmacist by creating an automated, patient-led medication grouping tool.

In general, there is a need in the art for technology that improves pharmacy efficiency. In their paper, Medication Overload: America's Other Drug Problem, authors Garber, J., and Brownlee, S. estimate that more than four in ten older adults take five or more prescription medications, triple the rate from twenty years ago. And nearly 20 percent take ten drugs or more. Brookline, MA: The Lown Institute. 2019. In addition to this huge increase in the number of prescriptions, pharmacies are now frontline providers of vaccines, e.g., flu and COVID, the latter of which will now be covered by insurance. These new offerings further strain pharmacy resources resulting in pharmacist shortages during an unprecedented time of polypharmacy. See, T. Murphy, Pharmacist shortages and heavy workloads challenge drugstores heading into their busy season, AP News, October 2023. Absent prescription alignment technology, for every individual prescription, the system must generate separate initial and reminder messages, which are predominantly electronic messages (text and/or e-mail), and receive and store customer responses. And due to their nature, these messages must be secured in accordance with HIPAA. These communications consume considerable processing and storage resources. Improvements to pharmacy systems that increases efficiency are sorely needed.

SUMMARY OF THE EMBODIMENTS

Aspects of the present disclosure allow for systematically grouping together all medications of the patient that would be eligible for a refill within a configurable window, and provide the list of such medications to the patient, in order to allow the patient to select an optimal grouping. This allows the pharmacy to proactively engage the patient in the medication grouping process prior to refill processing, while increasing prescription order size, when possible.

In a first exemplary embodiment, a patient-led prescription refill grouping system for improving pharmacy system efficiency by reducing electronic message transactions, includes: a processor configured to; determine whether a patient is projected to run out of a first prescription medication within a first window of time extending a first number of days ahead of a current day, in response to a determination that the patient is projected to run out of the first prescription medication within the first window of time, determine whether the patient is eligible to receive a refill of one or more second prescription medications within a second window of time extending a second number of days from a day when the patient is projected to run out of the first prescription medication, and send an electronic message based on contact information associated with the patient, wherein the sent electronic message includes a link to a patient portal, wherein, in response to a determination that the patient is eligible to receive the refill of the one or more second prescription medications within the second window of time, the patient portal provides an option of a refill order of the first prescription medication and the one or more second prescription medications, and receives a refill order of both of the first prescription and the one or more second prescriptions.

In a second exemplary embodiment, a patient-led prescription refill grouping system for improving pharmacy system efficiency by reducing electronic message transactions, includes: at least one processor configured to receive an electronic message including a link to a patient portal, in response to user input of information of a patient, access the patient portal, wherein the patient portal provides an option of a refill order of a first prescription medication and one or more second prescription medications, and input, through the patient portal, a refill order of one or both of the first prescription medication and the one or more second prescription medications, wherein the patient is projected to run out of the first prescription medication within a first window of time extending a first number of days ahead of a current day and the patient is eligible to receive a refill of the one or more second prescription medications within a second window of time extending a second number of days from a day when the patient is projected to run out of the first prescription medication.

In a third exemplary embodiment, a patient-led prescription refill grouping method for improving pharmacy system efficiency by reducing electronic message transactions, includes: determining whether a patient is projected to run out of a first prescription medication within a first window of time extending a first number of days ahead of a current day; in response to a determination that the patient is projected to run out of the first prescription medication within the first window of time, determining whether the patient is eligible to receive a refill of one or more second prescription medications within a second window of time extending a second number of days from a day when the patient is projected to run out of the first prescription medication, and sending an electronic message based on contact information associated with the patient, wherein the sent message includes a link to a patient portal, wherein, in response to a determination that the patient is eligible to receive the refill of the one or more second prescription medications within the second window of time, the patient portal provides an option of a refill order of the first prescription medication and the one or more second prescription medications and receives a refill order of both of the first prescription medication and the one or more second prescription medications.

In a fourth exemplary embodiment, a patient-led prescription refill grouping method for improving pharmacy system efficiency by reducing electronic message transactions, includes: receiving an electronic message including a link to a patient portal; in response to user input of information of a patient, accessing the patient portal, wherein the patient portal provides an option of a refill order of a first prescription medication and one or more second prescription medications; and inputting, through the patient portal, a refill order of one or both of the first prescription medication and the one or more second prescription medications, wherein the patient is projected to run out of the first prescription medication within a first window of time extending a first number of days ahead of a current day and the patient is eligible to receive a refill of the one or more second prescription medications within a second window of time extending a second number of days from a day when the patient is projected to run out of the first prescription medication.

Additional advantages and novel features of these aspects will be set forth in part in the description that follows, and in part will become more apparent to those skilled in the art upon examination of the following or upon learning by practice of the disclosure.

DETAILED DESCRIPTION

Aspects of the present disclosure are directed to addressing the above-described difficulties in current medication organization practices, as well as others. The disclosed patient-led prescription refill grouping methods and systems herein include, for example, but are not limited to, features relating to grouping a patient's medications based on projected refill dates and allowing the patient to select which of their medications are to be grouped for refill, which, among other advantages, may allow for improved efficiency in pharmacy operations, as well as added convenience to patients.

Figure 1:
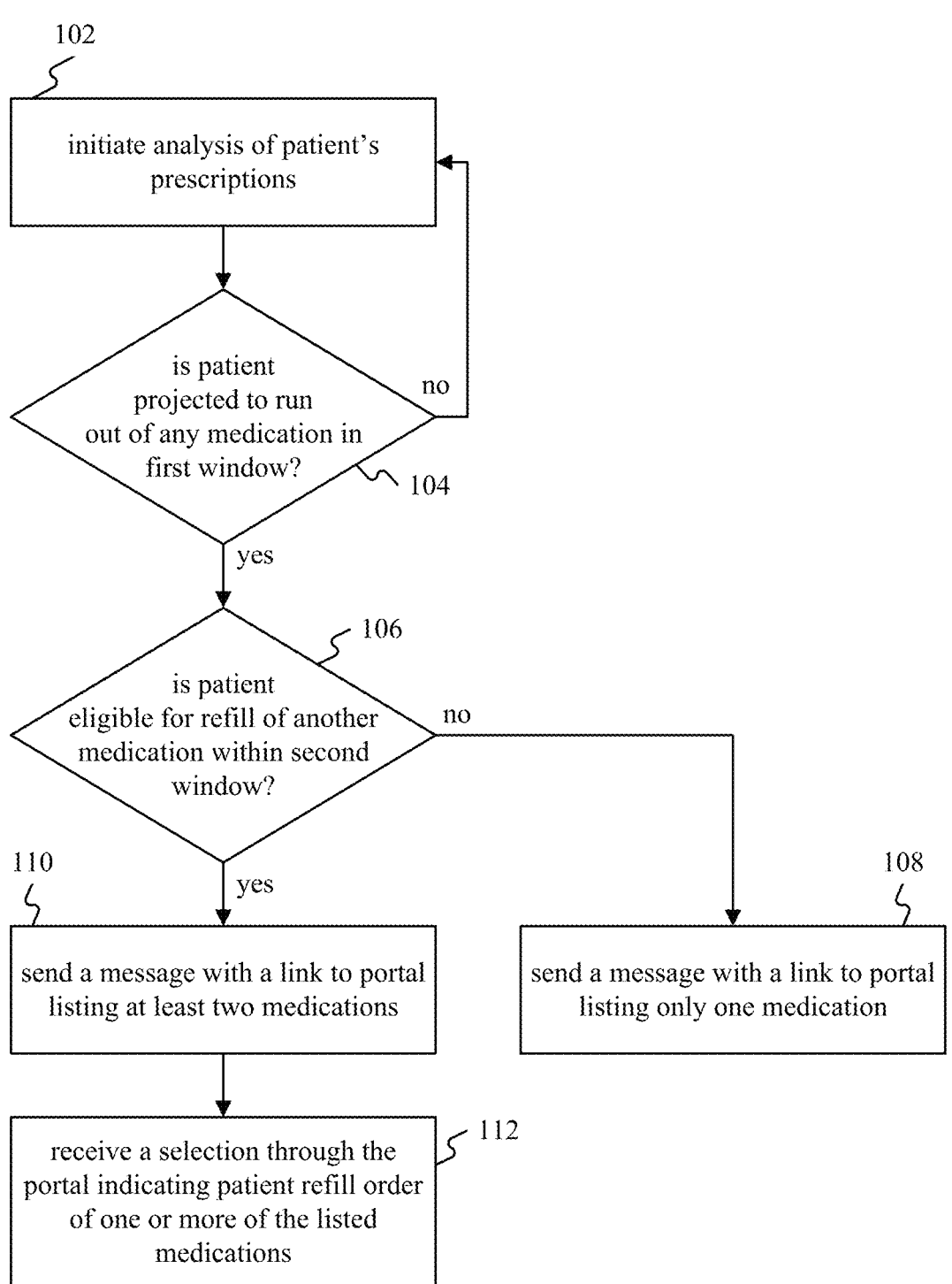
FIG. 1 shows a representative diagram showing example operations provided by one example implementation of a patient-led prescription refill grouping system, according to aspects of the present disclosure.

FIG. 1 shows a representative diagram showing example operations provided by one example implementation of a patient-led prescription refill grouping system, according to aspects of the present disclosure. In step 102, analysis of a patient's prescription profile may be initiated.

In one aspect of an example implementation of the refill grouping system, the prescription profile analysis may be initiated on a current day and may analyze a first window of days beginning on the following day after the current day.

Such an analysis may be triggered automatically for patient profiles stored in an example implementation of a prescription refill grouping system according to aspects of the present disclosure. For example, the analysis may be configured to run once a day or at another configured time interval.

In another example implementation, the analysis of step 102 may be configured to run on only a subset of the patient records stored in the prescription refill grouping system. For example, the analysis may only be run on patient records showing activity within the last year or within another configured time frame. The analysis of step 102 may also be triggered manually by an authorized administrator of the example implementation of a prescription refill grouping system according to aspects of the present disclosure.

Once the analysis of the patient's prescription profile is initiated in step 102, an example implementation of a prescription refill grouping system determines, in step 104, whether the patient is projected to run out of any medication within a certain number of days. For example, the certain number of days is configurable within the example implementation of the prescription refill grouping system as a first window. This determination may be made by the example implementation of the prescription refill grouping system based on the date of a last fill of each of the patient's medications, the amount of medication provided at the last fill, and the amount of medication taken per day.

In another aspect, the example implementation of the prescription refill grouping system may determine at step 104 whether the patient is projected to be eligible for a fill or a refill of a medication within the first window. In this aspect, the patient would not necessarily run out of any medication within the first window, but would instead be eligible for a fill or a refill within the first window.

For example, the patient's doctor may have written a new prescription for a new medication that is eligible to be filled. In this case, the next time the analysis of the patient's prescriptions is initiated, step 104 would determine that the patient is projected to be eligible for a fill of a medication within the first window because the new medication is eligible to be filled.

If it is determined that the patient is not projected to run out of any medications within the first window of days, the example implementation of the prescription refill grouping system may wait until the analysis is re-initiated at a later time, as shown by the NO branch from step 104 to step 102 in FIG. 1. On the other hand, if it is determined that the patient is projected to run out of a medication within the first window, or alternatively that the patient is projected to be eligible for a fill or a refill of a medication within the first window, the example implementation of the prescription refill grouping system moves to step 106.

In step 106, the example implementation of the prescription refill grouping system may determine whether the patient is eligible for a refill of another medication within a second window. The second window may be defined, for example, with reference to the date on which the patient was determined to run out of the medication in step 104.

For example, if the example implementation of the prescription refill grouping system determines in step 104 that the patient is projected to run out of a medication on day X, then in step 106 the example implementation of the prescription refill grouping system may determine whether the patient is eligible for a refill of another medication within the second window defined by day X+Y days, where Y may be configurable. That is, the first window may begin on day X when the patient is projected to run out of a medication in step 104 and the first window extends ahead of day X by Y days. In one example, Y may be set to a number of days that would make the second window the same as the first window used in step 104. In another example, Y may be set to a constant number of days, such as 4 days.

In one aspect, the example implementation of the prescription refill grouping system may determine that the patient is eligible for a refill of another medication if the patient is projected to run out of the other medication within the window of X+Y days. In another aspect, the example implementation of the prescription refill grouping system may determine that the patient is eligible for a refill of another medication if the patient is projected to have a utilization of the other medication above a preset configuration threshold within the window of X+Y.

If the example implementation of the prescription refill grouping system determines in step 106 that the patient is not eligible for a refill of another medication within the second window (NO branch from step 106), the example implementation of the prescription refill grouping system may send a message to the patient with a link to a patient portal listing only the medication identified in step 104, as indicated by step 108. For example, the message may be a reminder text or mobile message (e.g., SMS (short message service), MMS (multimedia message service), iMessage, instant messenger, In-App messages) or a reminder email sent to the patient's mobile phone or email address, respectively.

The message may indicate that the medication identified in step 104 is available for refill and/or the message my include a hyperlink to a patient portal. The hyperlink may open a web browser with the address of the patient portal or may open a pharmacy app installed on the patient's mobile device. The patient portal may require the patient to log in with credentials and/or enter the patient's name and date of birth, for example. Upon login, the patient portal may list all medications available for refill. In the example of step 108, only the medication identified in step 104 would be indicated as available.

The patient portal may also give the patient an option of having the medication delivered over mail and/or pharmacy location options where the medication may be picked up. The patient portal may also provide an option for the patient to indicate a day when the medication will be picked up.

Upon selecting among the various options available through the patient portal, the patient may submit their order to refill the medication identified in step 104. Upon submission of the order through the patient portal, the ordered medication may be filled at the location selected by the patient on or prior to the day selected by the patient, for example. In another example, the ordered medication may be shipped over mail, if the patient selected the mail order option in the patient portal.

On the other hand, if the example implementation of the prescription refill grouping system determines in step 106 that the patient is eligible to refill another medication within the second window (YES branch from step 106), the example implementation of the prescription refill grouping system may send a message to the patient in step 110. The message sent in step 110 may be similar to the reminder message described above in step 108, for example. In another aspect, the message sent in step 110 may be different from the message sent in step 108, for example by listing more than one medication that is available for refill. The message may be sent over one or more communication methods selected by the patient and/or the pharmacy, including over email, through a mobile app, or through a patient web portal.

The message sent in step 110 may give the patient an option to respond to the message and request all eligible medications to be ordered for refill. For example, if the message sent in step 110 is a text message, the message may include a list of all medications eligible for refill (including the medication identified in step 104 and one or more medications identified in step 106) and the text "Reply 1 to refill all."

In this example, the patient may respond with the number 1 to the text message and an order to refill all of the medications eligible for refill is submitted to the example implementation of the prescription refill grouping system. This aspect would allow a more convenient option for a patient to order all medications eligible for refill without having to log into the patient portal.

On the other hand, the message sent in step 110 may also include a hyperlink to the patient portal. Similarly to the link that may be sent in step 108, the hyperlink navigates to the patient portal and may require patient name, date of birth, and/or login credentials to log in. Once logged in, the patient portal shows a list of refillable medications.

The list may include a first medication identified in step 104 when the example implementation of the prescription refill grouping system determines that the patient is projected to run out of the first medication within the first window of time. The list may also include one or more second medications identified in step 106 when the example implementation of the prescription refill grouping system determines that the patient is eligible for refill(s) of the second medication(s) within the second window.

Each medication included in the list of refillable medications may be individually selectable in the patient portal. Accordingly, the patient may select one, some, or all of the medications in the list of refillable medications and submit their selection in step 112. That is, only the medications selected through the patient portal would be ordered for refill, allowing the patient to control their own medication grouping.

By allowing patients to select which refillable medications are to be ordered and grouped for refill, aspects of the example implementation of the prescription refill grouping system improve the efficiency of medication grouping by decreasing the labor burden on pharmacists and increasing the chances that medications will continue to be grouped. For example, under aspects of the example implementation of the prescription refill grouping system, pharmacists will no longer be required to determine whether patient medications should be grouped and will no longer be required to fill short-fill orders to achieve alignment.

Furthermore, because patients have more information regarding their own plans, habits, and medication usage than a pharmacist, a patient is best informed to determine whether grouping two or more particular medications would be helpful or efficient. For example, a patient that knows they are going to Florida during the winter and knows that an ointment medication is needed during the winter would not choose to include a refill of the ointment medication in a grouping to be refilled in the fall in Virginia, opting instead to fill the medication a bit later in Florida, ensuring that they will have the medication once they get there.

On the other hand, a patient going on international travel could be reminded by the patient portal that one or more medications are eligible for refill prior to their trip, and may select to group and refill those medications in order to ensure a full supply during their trip. Allowing patients to select which medications to group, for example through steps 110 and 112 of the described example implementation of the prescription refill grouping system, also improves the business efficiencies of the pharmacy by removing the added labor cost of short-filling prescriptions and by ensuring that only medications needed by the patient will be filled.

Figure 2:
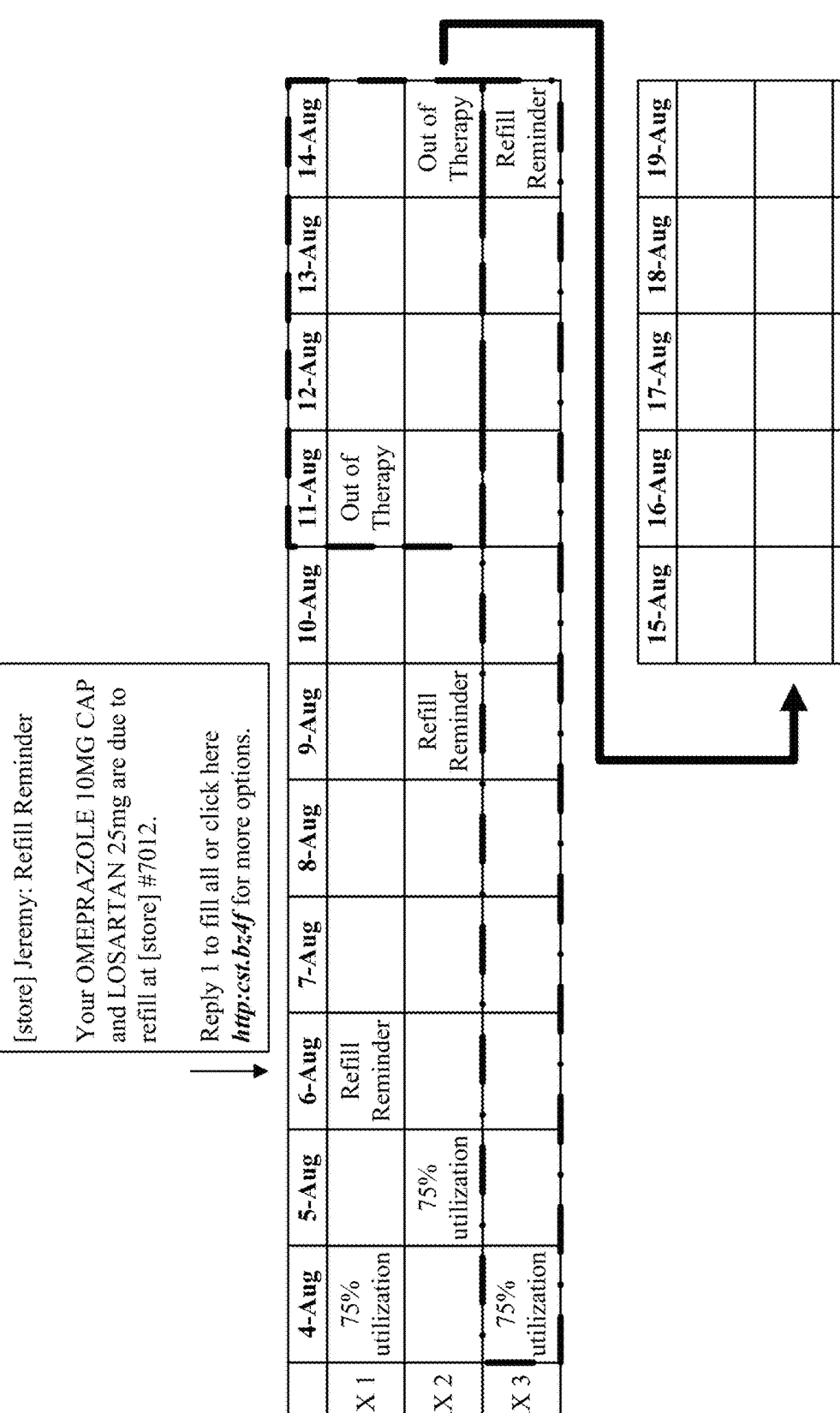
FIG. 2 shows a representative timeline indicating operations of one example implementation of a patient-led prescription refill grouping system, according to aspects of the present disclosure.

FIG. 2 shows an example of a timeline indicating the first window. Initially, a pharmacy configures how many days prior to a patient running out of a medication a message will be sent to the patient (Refill Reminder date in FIG. 2). In the example of FIG. 2, the pharmacy has selected 5 days.

In the example of FIG. 2, each day an automated process will run that looks forward 5 days for any medications that will run out for a patient. When the process runs on August 6 in the example of FIG. 2, the process looks 5 days ahead to August 11 and identifies RX 1 as out of therapy. This determination may correspond to step 104 in FIG. 1.

The determination may be made by the example implementation of the prescription ("RX") refill grouping system based on the date of a last fill of each of RX 1, RX 2, and RX 3, the amount of medication provided at the last fill, and the amount of medication taken per day. For example, the example implementation of the prescription refill grouping system may store information indicating that the patient's last fill of RX 1 was on July 12 and that the fill provided 30 days of medication. Based on this stored information, the example implementation of the prescription refill grouping system may determine that the patient is projected to run out of RX 1 on August 11.

As RX 1 is the earliest medication to run out among RX 1, RX 2, and RX 3 in the example of FIG. 2, determining that the patient is projected to run out of RX 1 on August 11 may correspond to the YES branch of step 104 in FIG. 1, which leads to the analysis of step 106 in FIG. 1. As part of the analysis of step 106, the example implementation of the prescription refill grouping system may determine whether the patient is eligible for a refill of another medication within a second window.

That is, when RX 1 is identified in the example of FIG. 2, a grouping process is initiated and will look ahead by a grouping window (i.e., second window) configured by the pharmacy, in this case three days. The grouping process will identify that RX2 will be out of therapy within this grouping window, which is indicated by a dashed line in FIG. 2.

The second window may be defined with respect to the day on which RX 1 is projected to run out, which is August 11 in the example of FIG. 2. For example, the second window may be defined as the day on which RX 1 is projected to run out plus three days. In this example, the second window may be defined as August 11 to August 14.

The analysis of step 106 determines, in the example of FIG. 2, that RX 2 is projected to run out on August 14. Because August 14 is within the second window and because running out of RX 2 means that RX 2 is eligible for refill, the analysis of step 106 proceeds to the YES branch in the example of FIG. 2. In this example, RX 1 and RX 2 are grouped for refill, as shown in FIG. 2.

As a result of the grouping process in FIG. 2, RX 1 and RX 2 are grouped into a single message delivered to the patient on August 6th. Additionally, RX 3, which will not be out of therapy within the grouping window, will have achieved the needed RX utilization (75% in the example of FIG. 2) to be a candidate for the patient to add to their order. With respect to RX 3, the example implementation of the prescription refill grouping system may determine that the patient's utilization rate of RX 3 reaches or exceeds 75% within the second window (i.e., grouping window). Other threshold utilization values may be configured, such as determining whether utilization of a medication is above 50% or 90% within the second window, for example.

In this aspect, a determination that the patient's utilization of RX 3 is projected to be above a preset threshold within the second window (for example, the window of August 11 to August 14 in FIG. 2) results in grouping RX 3 together with RX 1 in the group of refillable medications. However, if the patient of the example of FIG. 2 selects RX 1 and RX 2 to be grouped for refill, and not RX 3, such that RX 1 and RX 2 are refilled on August 6, the refill reminder for RX 3 will be sent on August 14.

As a result, the system in the example of FIG. 2 will combine RX 1 and RX 2 into the refill reminder and offer the patient the option to add RX 3 to the refill order by following the link in the refill reminder to a patient portal. FIG. 2 illustrates two conditions for grouping medications: (i) patient will be out of therapy within the grouping window or (ii) a configurable amount (75% in the example of FIG. 2) of utilization must be achieved of a previously filled medication. As described above with respect to FIG. 2, the refill reminder and associated grouping window analysis are triggered when it is determined that a patient will run out of medication within a configurable window of the current date.

Other aspects of patient attributes may be used to dictate an eligibility for grouping as well. For example, a patient who pays cash for their prescriptions may choose to fill their prescriptions at an earlier date before the needed utilization. The utilization of the prescription is a requirement that is in place to prevent early refill rejections from third party insurances as well as minimize prescription waste. Cash paying customers may override such a window.

As illustrated in the example of FIG. 2, the grouping analysis of the example implementation of the prescription refill grouping system does not require a short-fill of any medication in order to achieve the efficiencies and convenience of grouping medications for refill. This is achieved through the forward-looking grouping window used in the grouping analysis of step 106 of FIG. 1. By allowing the patient to group medications for refill using the forward-looking grouping analysis, the disadvantages of short-filling medications discussed above may be avoided, while capturing the improved patient experience and business efficiencies associated with medication alignment.

Figure 3:
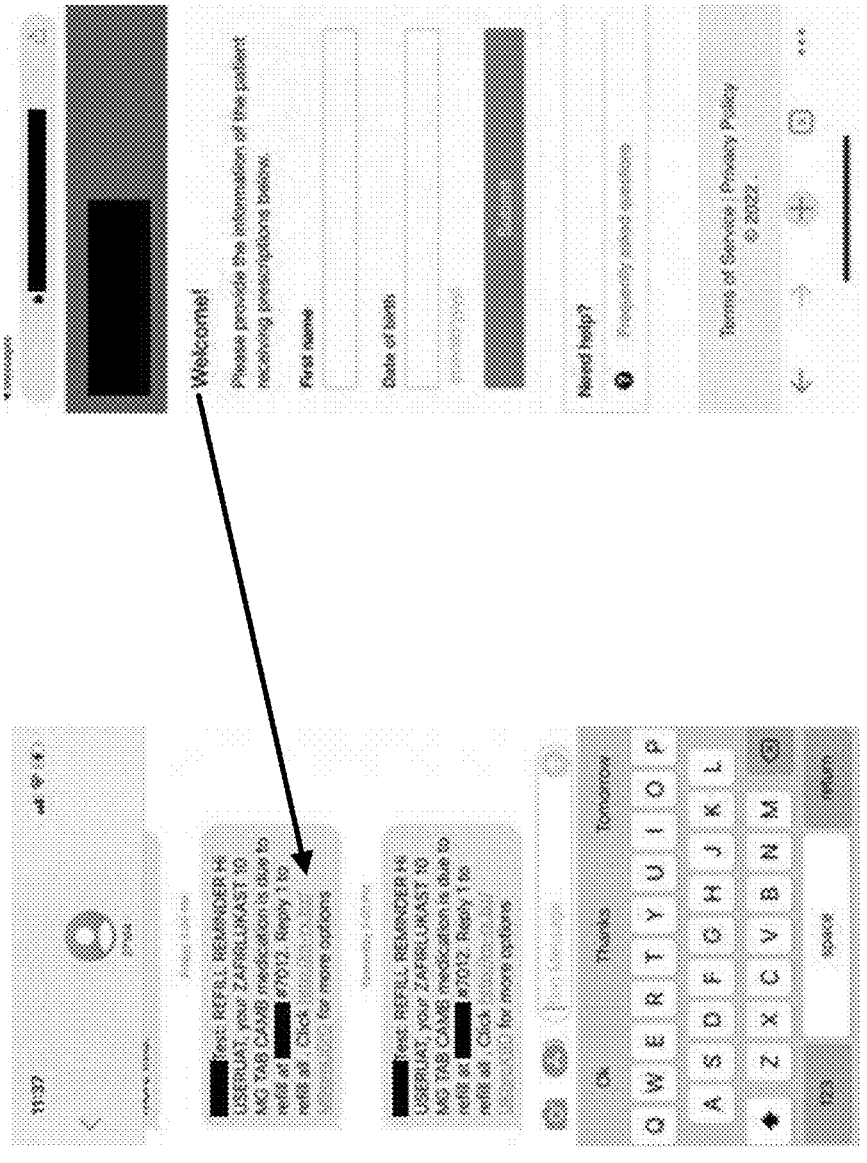
FIG. 3 shows a representative interface provided by one example implementation of a patient-led prescription refill grouping system, according to aspects of the present disclosure.

Once the analysis of step 106 is complete, a message (e.g., refill reminder) is sent based on contact information associated with the patient. FIG. 3 shows a representative interface used by the patient to receive the message and access a patient portal. When the contact information associated with the patient is a mobile phone number, the message may be a text message, as shown in the left-hand screenshot of FIG. 3.

The text message may list one or more of the medications eligible for refill and may include a hyperlink that allows access to a patient portal, as shown in FIG. 3. When the hyperlink is clicked, a patient portal may be opened either through a web browser of the mobile device or through an application installed on the mobile device. If the message was sent over email to an email address associated with the patient, the hyperlink may be provided in the email and likewise followed to a patient portal.

As shown in FIG. 3, the patient portal may include a log in screen that requires the patient's name and date of birth. Other credentials or patient information may also be required to log into the patient portal, for example. Once the patient name and/or credentials are entered, a screen such as the one shown on the left-hand side of FIG. 4 may be displayed.

Figure 4:
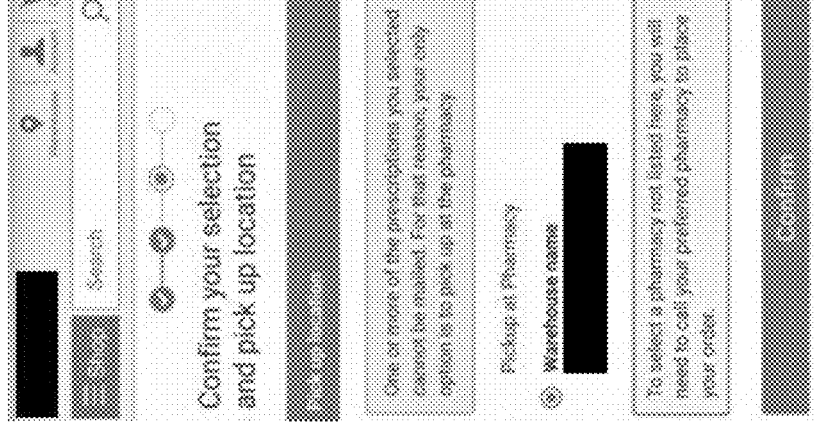
FIG. 4 shows a representative interface of a patient portal provided by one example implementation of a patient-led prescription refill grouping system, according to aspects of the present disclosure.
Figure 4:
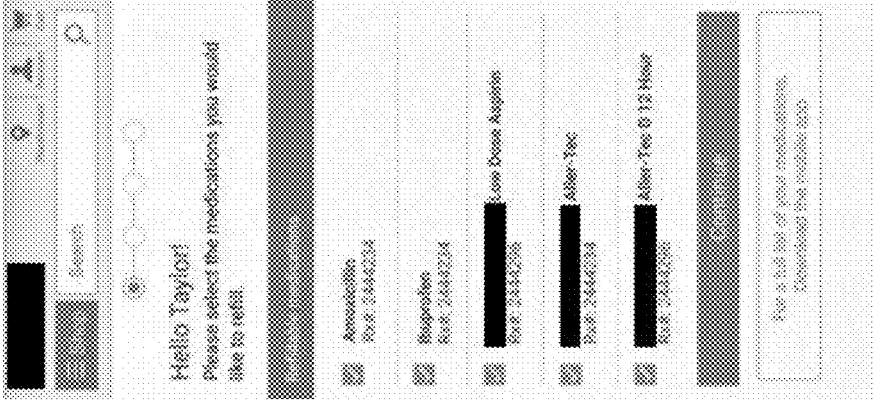

The patient portal lists the refillable medications determined as a result of steps 104 and 106 in FIG. 1. Each of the listed refillable medications is individually selectable by the patient in the patient portal, for example by clicking a selection box next to the medication, as shown in FIG. 4. As described above, this selection screen in the patient portal allows for a patient-led refill grouping system by allowing the patient to select which medications will be refilled together. The patient may make such selections on patient-specific information and preferences, including projected use of the medication, upcoming travel, etc.

One the selections are made in the medication selection screen, such as the one shown on the left hand side of FIG. 4, a confirmation screen such as the one shown on the right hand side of FIG. 4 may be displayed. The confirmation screen shown in FIG. 4 confirms a location where the refill order may be picked up.

Aspects of the example implementation of the prescription refill grouping system may also allow the patient, via the patient portal, to select a pickup location for the refill order, select for the refill order to be mailed to the patient, and/or select a day on which the refill order will be picked up. The refill order confirmation shown in FIG. 4 is for a full refill of the selected medications, not a short-fill order. As described above, the example implementation of the prescription refill grouping system avoids short-fill orders of any medications through the forward-looking grouping analysis of step 106 of FIG. 1.

In one aspect of the example implementation of the prescription refill grouping system, plural patients may be tied to the same patient portal account and mobile phone number/email address. For example, a parent may configure their mobile phone number as the contact information for themselves, as well as their children and spouse.

In this case, the prescription analysis described in FIG. 1 is performed with respect to all patients tied to the patient portal account. For example, the determination of step 104 may determine that a child is projected to run out of a medication in the first window, while the determination of step 106 may determine that the parent is eligible for a refill of another medication in the second window.

Based on the determinations of steps 104 and 106, the patient portal screen listing the refillable medications would list both the child's medication and the parent's medication and would allow these medications to be selected for grouping, despite not being associated with the same patient. In another aspect of the example implementation of the prescription refill grouping system, the patient portal allows the patient to schedule a pharmacy appointment on the day selected for pickup of the refill order. The pharmacy appointment may be one or more of (i) receiving immunization, (ii) insurance counseling, or (iii) point of care testing, for example.

The following example highlights features of one or more embodiments described herein and the resulting benefits. In a limited rollout of the functionality, applied to 2,074 actual employees and their families across 4 different pharmacy locations of the same chain. In implementation, in a first grouping job, an initial message is sent to a patient if they have even 1 prescription coming due since the existence of 1 prescription coming due triggers the secondary grouping job which looks for other additional upcoming medications which may be due (within the same family). In some cases, a patient may already have their medications aligned, so while they may not need to be grouped, that patient will now have a consolidated, single, clean text message.

In an initial AM test run against the 2,074 actual employees, the system ultimately sent out text messages to 115 patients, who accounted for a total of 160 prescriptions, having an order size of 1.4. The following statistics highlight efficiencies of the process.

17 of the 115 orders (14.9%) successfully grouped together orders that would have otherwise been separated.

18 of the orders (15.6%) had prescriptions that would have messaged a patient separately, for each prescription, instead, a single, clean, text was sent.

Instead of sending 160 text messages, one for each prescriptions, the system sent 115, reducing the text messages sent to patients by 28%.

This system grouping feature impacted over 30% of messages.

The following patient-specific example is indicative of how the embodied system and process implement efficiencies, saving patients' time and creating efficiency and convenience. This patient A had 1 prescription due to fill the day after the initial AM test run. Patient A also had 3 other prescriptions that were due on July $4^{th}$ (a day when the pharmacies are closed). Without the benefit of the embodied grouping process, patient A would have run out of 3 medications on a day when the pharmacy is closed. Holidays are a very strained time for pharmacies, and the embodiment grouping system was able to pull forward those 3 prescriptions for patient A and add with the triggering prescription due the next day into a single bundled message. This means no last minute call from a patient to scramble to fill their meds. This means 1 text message, 1 point of sale transaction, 1 encounter with the pharmacist, 1 bag, and 1 trip to the pharmacy.

Figure 5:
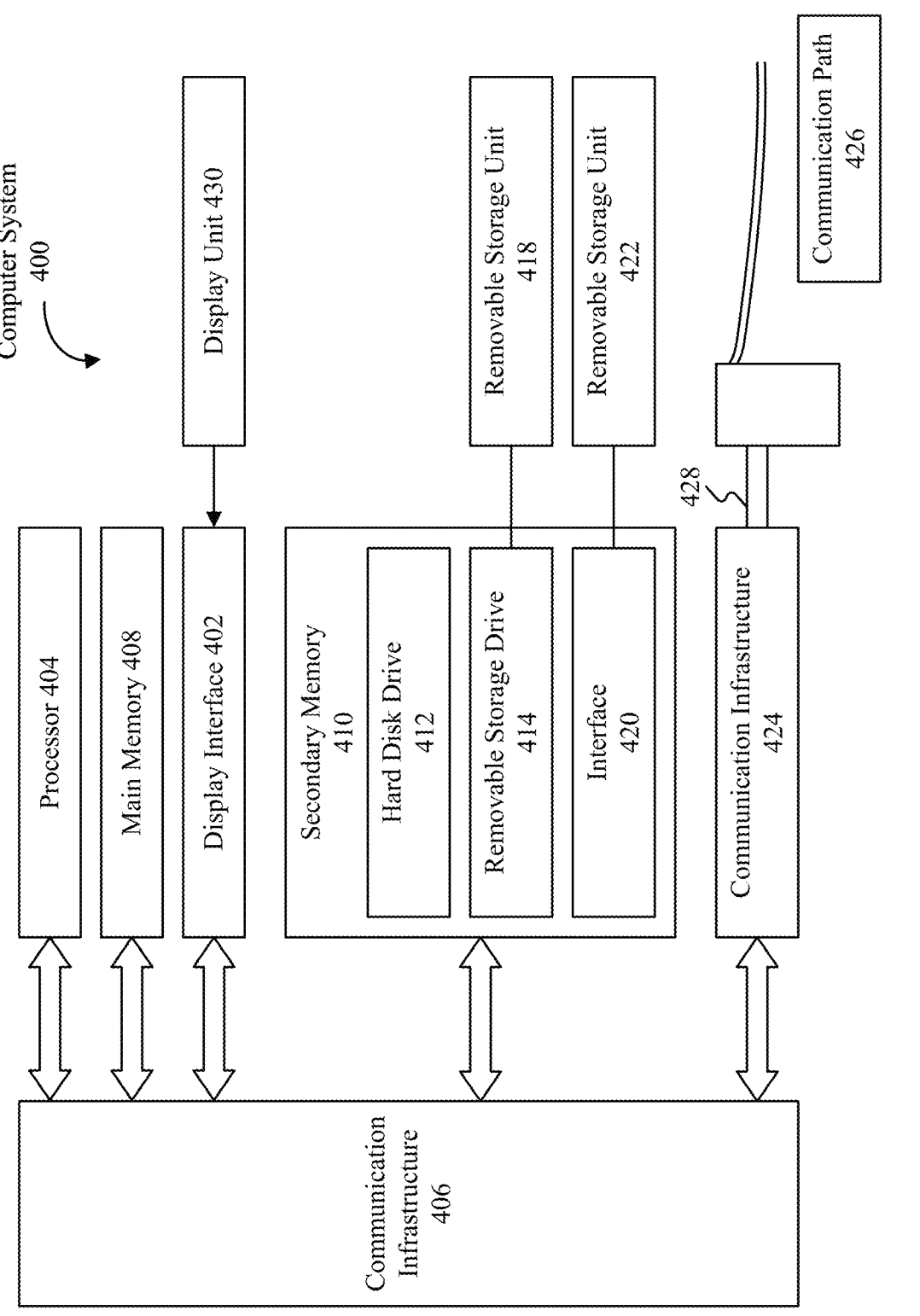
FIG. 5 shows a representative diagram of various features an example computer system capable of carrying out various functionality of an example patient-led prescription refill grouping system in accordance with aspects of the present disclosure.

Aspects of the present disclosure may be implemented using hardware, software, or a combination thereof and may be implemented in one or more computer systems or other processing systems. In an aspect of the present disclosure, features are directed toward one or more computer systems capable of carrying out the functionality described herein. Various aspects of an example of such a computer system (400) are shown in FIG. 5.

Computer system (400) includes one or more processors, such as processor (404), including processing circuitry. The processor (404) may be coupled to a communication infrastructure (406) (e.g., a communications bus, cross-over bar, or network). Various software aspects are described in terms of this example computer system. After reading this description, it will become apparent to a person skilled in the relevant art(s) how to implement aspects hereof using other computer systems and/or architectures.

Computer system 400 may include a display interface (402) that forwards graphics, text, and other data from the communication infrastructure (406) (or from a frame buffer not shown) for display on a display unit (430). Computer system 400 may include a main memory (408), such as random access memory (RAM), and may also include a secondary memory (410). The secondary memory (410) may include, for example, a hard disk drive (412) and/or a removable storage drive (414), representing a floppy disk drive, a magnetic tape drive, an optical disk drive, etc. The removable storage drive (414) may read from and/or write to a removable storage unit (418) in a well-known manner. Removable storage unit (418) represents a floppy disk, magnetic tape, optical disk, etc., which may be read by and written to removable storage drive (414). As will be appreciated, the removable storage unit (418) may include a computer usable storage medium having stored therein computer software and/or data.

Alternative aspects may include secondary memory (410) and may include other similar devices for allowing computer programs or other instructions to be loaded into computer system (400). Such devices may include, for example, a removable storage unit (422) and an interface (420). Examples of such devices may include a program cartridge and cartridge interface (such as that found in video game devices), a removable memory chip (such as an erasable programmable read only memory (EPROM), or programmable read only memory (PROM)) and associated socket, and other removable storage units (422) and interfaces (420), which allow software and data to be transferred from the removable storage unit (422) to computer system (400).

Computer system (400) may also include a communications interface (424). Communications interface (424) may allow software and data to be transferred among computer system (400) and external devices. Examples of communications interface (424) may include a modem, a network interface (such as an Ethernet card), a communications port, a Personal Computer Memory Card International Association (PCMCIA) slot and card, etc. Software and data transferred via communications interface (424) may be in the form of non-transitory signals (428) which may be electronic, electromagnetic, optical, or other signals capable of being received by communications interface (424). These signals (428) may be provided to communications interface (424) via a communications path (e.g., channel) (426). This path (426) may carry signals (428) and may be implemented using wire or cable, fiber optics, a telephone line, a cellular link, a radio frequency (RF) link and/or other communications channels. As used herein, the terms "computer program medium" and "computer usable medium" refer generally to media such as a removable storage drive (414), a hard disk installed in hard disk drive (412), and/or signals (428). These computer program products may provide software to the computer system (400). Aspects of the present disclosure are directed to such computer program products.

Computer programs (also referred to as computer control logic) may be stored in main memory (408) and/or secondary memory (410). Computer programs may also be received via communications interface (424). Such computer programs, when executed, may enable the computer system (400) to perform the features in accordance with various aspects discussed herein. In particular, the computer programs, when executed, may enable the processor (404) to perform the features in accordance with aspects of the present disclosure. Accordingly, such computer programs may represent controllers of the computer system 400.

Where aspects of the present disclosure may be implemented using software, the software may be stored in a computer program product and loaded into computer system (400) using removable storage drive (414), hard disk drive (412), or communications interface (424). The control logic (software), when executed by the processor (404), may cause the processor (404) to perform the functions described herein. In another aspect of the present disclosure, the system may be implemented primarily in hardware using, for example, hardware components, such as application specific integrated circuits (ASICs). Implementation of the hardware state machine so as to perform the functions described herein will be apparent to persons skilled in the relevant art(s).

For example, the computer system (400) may implement the processing shown in FIG. 1. In one aspect, steps 102 through 106 of FIG. 1 may be performed by processor (404) executing program code (i.e., computer-readable instructions) that may be loaded from main memory (408), secondary memory (410), removable storage units (418 and 422), or a combination thereof.

Furthermore, the patient medication and prescription data that is to be analyzed in steps 102 through 106 of FIG. 1 may likewise be stored in main memory (408), secondary memory (410), removable storage units (418 and 422), or a combination thereof. The patient medication and prescription data may be accessed by the processor (408) as needed to perform steps 102 through 106.

Furthermore, the sending of messages in steps 108 and 110, as well as the receiving a selection in step 112 of FIG. 1 may be implemented through the communication infrastructure (406 and 424) and communication path (426). That is, upon completion of steps 102 through 106 by processor (404), a message may be generated and transmitted through the communication infrastructure (406 and 424) and communication path (426) and a patient selection may be received through the communication infrastructure (406 and 424) and communication path (426).

Display interface (402) and display unit (430) may allow an authorized user of the computer system (400), such as pharmacy staff, to configure or update features of the system. For example, a number of days in the first window of step 104 or the second window of step 106 may be configured through display interface (402) and display unit (430). Various other configurable variables of the example implementation of the prescription refill grouping system may be set or updated through computer system (400).

Additionally, various portions of computer system (400) may be disposed in different locations. In one aspect, the computer system (400) may be disposed in a pharmacy or in a central pharmacy management location. In another aspect, the processor (404) and at least one of main memory (408), secondary memory (410), removable storage units (418 and 422) may be part of a prescription refill grouping service, which may access pharmacy data and provide the prescription refill grouping service based on the pharmacy data to patients of the pharmacy.

In yet another variation, aspects of the present disclosure may be implemented using a combination of both hardware and software.

Figure 6:
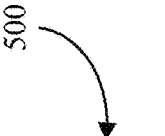
FIG. 6 shows a representative block diagram of various system components, capable of being used in an example implementation of a patient-led prescription refill grouping system in accordance with aspects of the present disclosure.
Figure 6:
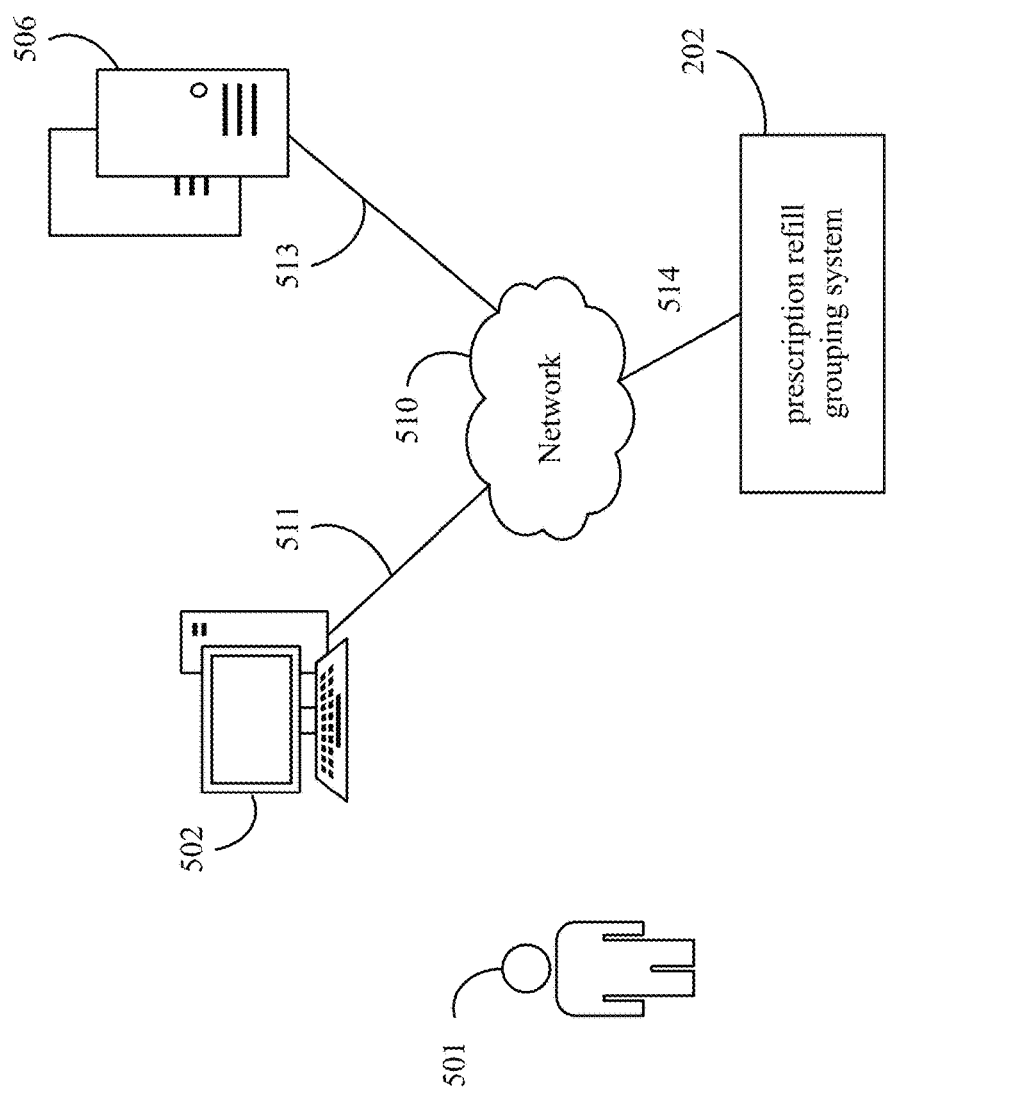

FIG. 6 is a block diagram of various example system components, for use in accordance with aspects of the present disclosure. FIG. 6 shows a communication system (500) usable in accordance with aspects hereof. The communication system (500) shown in FIG. 6 includes one or more accessors (501) (also referred to interchangeably herein as one or more "users") and one or more terminals (502). In one aspect, data for use in accordance with aspects of the present disclosure is, for example, input and/or accessed by accessor (501) via terminal (502), such as personal computers (PCs), command issuing devices including Graphical User Interfaces (GUIs), minicomputers, mainframe computers, microcomputers, telephonic devices, or wireless devices, such as personal digital assistants (PDAs), smart phones, frequency operated button (FOB), and/or other hand-held wireless devices (optionally coupled to or via a server (506), such as a PC, minicomputer, mainframe computer, microcomputer, or other device having a processor and a repository for data and/or connection to a repository for data), via, for example, a network (510), such as the Internet or an intranet, and couplings (511, 513, 514). The couplings (511, 513, 514) may include, for example, wired, wireless, or fiber optic links. In one example implementation of a prescription refill grouping system, terminal (502) may be coupled to network (510) via coupling (511) and therefore be able to receive input data from user (501), such that the user (501) may be able to selectively control and/or carry out various operations of a prescription refill grouping system (202), in accordance with aspects of the present disclosure.

In one aspect, the user (501) may be an administrator of the prescription refill grouping system (202) and may configure the prescription refill grouping system (202) through the terminal (502). As described above, configurable settings of the prescription refill grouping system (202) may include the length of the first window, the length of the second window, as well as the options provided to the patient through messaging and the patient portal.

In another aspect, the user (501) may be the patient, which may receive messages from the prescription refill grouping system (202) through the network (510) and may input refill grouping selections through the terminal (502). As noted above, the prescription refill grouping system (202) may be disposed at a single site or may be distributed across multiple sites such that some or all of the processing shown in FIG. 1 is supported by patient data that is accessed from another location.

While the aspects described herein have been described in conjunction with the example aspects outlined above, various alternatives, modifications, variations, improvements, and/or substantial equivalents, whether known or that are or may be presently unforeseen, may become apparent to those having at least ordinary skill in the art. Accordingly, the example aspects, as set forth above, are intended to be illustrative, not limiting. Various changes may be made without departing from the spirit and scope of the disclosure. Therefore, the disclosure is intended to embrace all known or later-developed alternatives, modifications, variations, improvements, and/or substantial equivalents.

Thus, the claims are not intended to be limited to the aspects shown herein, but are to be accorded the full scope consistent with the language of the claims, wherein reference to an element in the singular is not intended to mean "one and only one" unless specifically so stated, but rather "one or more." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

Further, the word "example" is used herein to mean "serving as an example, instance, or illustration." Any aspect described herein as "example" is not necessarily to be construed as preferred or advantageous over other aspects. Unless specifically stated otherwise, the term "some" refers to one or more. Combinations such as "at least one of A, B, or C," "at least one of A, B, and C," and "A, B, C, or any combination thereof" include any combination of A, B, and/or C, and may include multiples of A, multiples of B, or multiples of C. Specifically, combinations such as "at least one of A, B, or C," "at least one of A, B, and C," and "A, B, C, or any combination thereof" may be A only, B only, C only, A and B, A and C, B and C, or A and B and C, where any such combinations may contain one or more member or members of A, B, or C. Nothing disclosed herein is intended to be dedicated to the public regardless of whether such disclosure is explicitly recited in the claims.

We claim:

1. A patient-led prescription refill grouping system for improving pharmacy system efficiency and reducing electronic storage resources by reducing a volume of electronic message transactions, comprising:

a processor configured to analyze a patient profile stored in an electronic memory of the pharmacy system to automatically determine whether a patient is projected to run out of a first prescription medication within a first window of time extending a first number of days ahead of a current day, in response to a determination that the patient is projected to run out of the first prescription medication within the first window of time, trigger a second analysis of the patient profile to automatically determine whether the patient is eligible to receive a refill of one or more second prescription medications within a second window of time extending a second number of days from a day when the patient is projected to run out of the first prescription medication, automatically determine whether contact information associated with the patient is associated with another patient;

in response to a determination that the contact information is associated with the another patient, trigger analysis of a patient profile of the other patient stored in the electronic memory of the pharmacy system to automatically determine whether the other patient is eligible to receive a refill of a third prescription medication within the second window of time; and automatically generate and send a single electronic message based on the contact information associated with the patient, wherein the single sent electronic message includes a link to an electronically-accessible patient portal, wherein, in response to a determination that the patient is eligible to receive the refill of the one or more second prescription medications within the second window of time and in response to a determination that the other patient is eligible to receive the refill of the third prescription medication within the second window of time, the patient portal i. provides an option of a refill order of the first prescription medication and the one or more second prescription medications, ii. provides an option of a refill order of the first prescription medication and the third prescription medication, iii. provides an option of a refill order of the first prescription medication, the one or more second prescription medications and the third prescription medication, iv. receives a refill order selected from the group consisting of i, ii or iii;

thereby reducing electronic storage resources by reducing the volume of electronic message transactions between the patient and the pharmacy system.

2. The system according to claim 1, wherein the first number of days of the first window of time and the second number of days of the second window of time are preset in the system.

3. The system according to claim 1, wherein the processor is configured to determine whether the patient is projected to run out of the first prescription medication within the first window of time once each day.

4. The system according to claim 1, wherein the patient portal provides an option to receive the refill order via mail.

5. The system according to claim 1, wherein the patient portal provides an option to select a pharmacy location at which to pick up the refill order.

6. The system according to claim 1, wherein the patient portal provides an option to pick up the refill order on a selected day.

7. The system according to claim 6, wherein the patient portal provides an option to schedule a pharmacy appointment on the selected day for one or more of (i) receiving immunization, (ii) insurance counseling, or (iii) point of care testing.

8. The system according to claim 1, wherein the processor determines that the patient is eligible to receive the refill of the one or more second prescription medications within the second window of time when the patient is projected to run out of the one or more second prescription medications within the second window of time.

9. The system according to claim 1, wherein the processor determines that the patient is eligible to receive the refill of the one or more second prescription medications within the second window of time when the patient's utilization of a previously filled order of the one or more second prescription medications is projected to be above a utilization threshold within the second window of time.

10. The system according to claim 1, wherein the processor is configured to send the electronic message a third number of days prior to the day when the patient is projected to run out of the first prescription medication, wherein the third number of days is configurable by the patient in the patient portal.

11. The system according to claim 1, further comprising sending a reminder electronic message when the refill order is not received within a fourth number of days after sending the electronic message.

12. The system according to claim 1, wherein, in response to a determination that the patient is eligible to receive the refill of the one or more second prescription medications within the second window of time, the sent message lists the first prescription medication and the one or more second prescription medications and provides an option to respond to the electronic message to order a refill of both the first prescription medication and the one or more second prescription medications without accessing the patient portal.

13. A patient-led prescription refill grouping method for improving pharmacy system efficiency and reducing electronic storage resources by reducing a volume of, electronic message transactions, comprising:

automatically determining, by a processing system, whether a patient is projected to run out of a first prescription medication within a first window of time extending a first number of days ahead of a current day by analyzing a patient profile stored in an electronic memory of the pharmacy system;

in response to a determination that the patient is projected to run out of the first prescription medication within the first window of time, triggering a second analysis of the patient profile and

determining whether the patient is eligible to receive a refill of one or more second prescription medications within a second window of time extending a second number of days from a day when the patient is projected to run out of the first prescription medication, determining whether contact information associated with the patient is associated with another patient;

in response to a determining that the contact information is associated with the another patient, triggering analysis of a patient profile of the other patient stored in the electronic memory of the pharmacy system and automatically determining whether the other patient is eligible to receive a refill of a third prescription medication within the second window of time and automatically generate and send a single electronic message based on the contact information associated with the patient, wherein the single sent electronic message includes a link to an electronically-accessible patient portal, wherein, in response to a determination that the patient is eligible to receive the refill of the one or more second prescription medications within the second window of time and in response to a determination that the other patient is eligible to receive the refill of the third prescription medication within the second window of time, i. providing, by the patient portal, an option of a refill order of the first prescription medication and the one or more second prescription medications and ii. providing, by the patient portal, an option of a refill order of the first prescription medication and the third prescription medication, iii. providing, by the patient portal, an option of a refill order of the first prescription medication, the one or more second prescription medications and the third prescription medication, iv. receiving, via the patient portal, a refill order selected from the group consisting of i, ii or iii;

thereby reducing electronic storage resources by reducing the volume of electronic message transactions between the patient and the pharmacy system.

* * * * *